(12) United States Patent
Mistrik et al.

(10) Patent No.: US 12,283,472 B2
(45) Date of Patent: Apr. 22, 2025

(54) IDENTIFICATION OF CHEMICAL STRUCTURES

(71) Applicant: HighChem s.r.o., Bratislava (SK)

(72) Inventors: Robert Mistrik, Bratislava (SK);
Michal Raab, Bratislava (SK)

(73) Assignee: HighChem s.r.o., Bratislava (SK)

( * ) Notice: Subject to any disclaimer, the term of this patent is extended or adjusted under 35 U.S.C. 154(b) by 1059 days.

(21) Appl. No.: 15/734,215

(22) PCT Filed: Jun. 3, 2019

(86) PCT No.: PCT/EP2019/064362
§ 371 (c)(1),
(2) Date: Dec. 1, 2020

(87) PCT Pub. No.: WO2019/229270
PCT Pub. Date: Dec. 5, 2019

(65) Prior Publication Data
US 2021/0210317 A1    Jul. 8, 2021

(30) Foreign Application Priority Data
Jun. 1, 2018    (GB) ...................... 1809018

(51) Int. Cl.
*H01J 49/00*    (2006.01)
*G16C 20/40*    (2019.01)
*G16C 20/80*    (2019.01)

(52) U.S. Cl.
CPC .......... *H01J 49/0036* (2013.01); *G16C 20/40* (2019.02); *G16C 20/80* (2019.02)

(58) Field of Classification Search
None
See application file for complete search history.

(56) References Cited

U.S. PATENT DOCUMENTS

| 7,197,402 B2 | 3/2007 | Mistrik |
| 2004/0024539 A1 | 2/2004 | Gard et al. |
| 2013/0306857 A1 | 11/2013 | Yamaguchi |

OTHER PUBLICATIONS

Lynn et al., "Metabolite Identification for Mass Spectrometry-Based Metabolomics Using Multiple Types of Correlated Ion Information," Anal. Chem. 2015, 87:2143-2151, with 14 pages of Supporting Information. (Year: 2015).*
Anonymous, "MassBank User's Manual—Version 2.4" (2012), 33 pages. URL: https://usermanual.wiki/Document/UserManualen.1740742609/help.
Lebedev et al., "New Computer Aided Methods for Revealing Structural Features of Unknown Compounds Using Low Resolution Mass Spectra", Journal of Chemical Information and Computer Sciences, 1998, vol. 38 (3), pp. 410-419.

(Continued)

*Primary Examiner* — Kaijiang Zhang
(74) *Attorney, Agent, or Firm* — Klarquist Sparkman, LLP

(57) ABSTRACT

A method for analysing mass spectral data of a substance comprises identifying a plurality of candidate chemical structure sets for the substance, each set being identified using one or more respective properties of the mass spectral data. The method comprises determining a level of similarity between candidate chemical structures from different candidate chemical structure sets, so as to determine a likelihood that one of the candidate chemical structures represents the substance.

16 Claims, 8 Drawing Sheets

(56) References Cited

OTHER PUBLICATIONS

Lynn et al., "Metabolite Identification for Mass Spectrometry-Based Metabolomics Using Multiple Types of Correlated Ion Information", Analytical Chemistry, 2014, vol. 87 (4), pp. 2143-2151.

* cited by examiner

| | | Structure Similarity | Spectral Similarity | Partial Score |
|---|---|---|---|---|
| (a) |  | (i,a) 100% | (a) 75.3% | 1 *0.753² |
| (b) |  | (i,b) 76% | (b) 71.5% | 0.76 *0.715² |
| (c) |  | (i,c) 40% | (c) 47.0% | 0.4 *0.47² |
| | | | Partial Score Sum | 0.679 |

(i)

IDENTIFICATION OF CHEMICAL STRUCTURES

TECHNICAL FIELD OF THE DISCLOSURE

The disclosure relates to a method for identifying the chemical structure of a substance using mass spectral data.

BACKGROUND TO THE INVENTION

Identification of samples containing substances is a frequent goal in analytical chemistry. Mass spectrometry is often used for identification due to its high sensitivity and relatively inexpensive experimental setup. Typical scenarios in which mass spectrometry is used include metabolomics, proteomics, natural substance identification and pharmaceuticals, as well as many other related fields.

Library searches are often used in identification experiments. Library searches require a reference mass spectral library that contains structurally characterised compounds of interest together with their fragmentation spectra, known as the spectral fingerprint (McLafferty et al., "Unknown Identification Using Reference Mass Spectra. Quality Evaluation of Databases", J. Am. Soc. Mass Spectrom., 1999, 10 (12), 1229-1240). When the mass spectral data for the unknown and the reference compound are obtained under the same experimental conditions, identification is reduced to a search in a spectral database for an identical spectrum.

In practice, however, identification is complicated by the fact that exact experimental conditions of spectral acquisition are not reproducible for many reasons (Stein, "Estimating Probabilities of Correct Identification from Results of Mass spectral library Searches", J. Am. Soc. Mass Spectrom., 1994, 5 (4), p 316-323; Weinmann et al., "Screening for Drugs in Serum by Electrospray Ionization/Collision-Induced Dissociation and Library Searching", J. Am. Soc. Mass Spectrom., 1999, 10 (10), p 1028-1037; Bristow et al., "Evaluation of Protocols for Reproducible Electrospray in-Source Collisionally Induced Dissociation on Various Liquid Chromatography/Mass Spectrometry Instruments and the Development of Spectral Libraries", Rapid Comm. Mass Spectrom., 2002, 16 (24), p 2374-2386; Bogusz et al., "Poor Reproducibility of in-Source Collisional Atmospheric Pressure Ionization Mass Spectra of Toxicologically Relevant Drugs", J. Chromatog. A, 1999, 844 (1-2), p 409-418; Gika et al., "Within-Day Reproducibility of an HPLC-MS-Based Method for Metabonomic Analysis: Application to Human Urine", J. Proteome Res., 2007, 6 (8), p 3291-3303).

The irreproducibility of experimental conditions means that no two spectra are identical and the degree of similarity between an unknown (query) spectrum and a reference (library) spectrum may be represented by a continuous measure of probability (or a match factor) rather than a binary indication of a match (Oberacher et al., "Testing an Alternative Search Algorithm for Compound Identification with the 'Wiley Registry of Tandem Mass Spectral Data, MSforID'", J. Mass Spectrom., 2013, 48 (4), p 497-504; Stein and Scott, "Optimization and Testing of Mass spectral library Search Algorithms for Compound Identification", J. Am. Soc. Mass Spectrom., 1994, 5 (9), p 859-866).

Several approaches have been proposed that seek to address these difficulties and enhance searching for a sample spectrum within a library. For instance, Sheldon et al., "Determination of Ion Structures in Structurally Related Compounds Using Precursor Ion Fingerprinting", J. Am. Soc. Mass Spectrom., 2009, 20 (3), p 370-376 and Mistrik (U.S. Pat. No. 7,197,402 B2) describe obtaining substructures from multiple tandem mass spectral searches and then attempting to combine the identified substructures into a larger structure. Meanwhile, Yamaguchi (US-2013/0306857 A1) uses a molecular weight to produce potential chemical structures and then predicts the dissociation patterns of the candidates for comparison with actual measurements from $MS^n$ spectra. Demuth et al., "Spectral Similarity versus Structural Similarity: Mass Spectrometry", Analytica Chimica Acta, 2004, 516 (1-2), p 75-85 proposes an alternative approach involving calculating how pre-defined features of mass spectral data correlate with structural features of a substance.

The accuracy of a proposed structure returned by such searches may be assessed and quantified by comparing the "unknown" substance and the substance identified by the search. For instance, a measure of the degree of similarity between the chemical structure of the "unknown" substance and the chemical structure proposed by the library search may be used to indicate the quality of the identification. The chemical structure of the "unknown" substance may be independently validated using analytical techniques other than mass spectrometry, such as nuclear magnetic resonance (NMR).

The comprehensiveness of spectral libraries is ultimately determined by the availability of well-characterised chemical standards and their predisposition to producing high-quality fragmentation spectra. As many substances are inherently difficult to characterise using mass spectrometry, methods have been proposed that attempt to combine mass spectral data with structural information from independent experimental methods, such as NMR, in an attempt to reduce the effect on identification of poor quality mass spectra (Dias et al., "Current and Future Perspectives on the Structural Identification of Small Molecules in Biological Systems", 2016, Metabolites 6 (4), 46).

Despite significant advances in the field of library searching, interpreting the mass spectrum of an unknown compound remains a non-trivial and computationally intensive task that usually requires dedicated software systems (Computer-Assisted Structure Elucidation, CASE) and considerable expertise to arrive at plausible conclusions. Moreover, even when such systems are employed, library searches are still limited by the size of the reference mass spectral library, since the largest current reference database of mass spectra contains approximately 243,000 unique chemical compounds (www.nist.novisrd/nist-standard-reference-database-1a-v14) and many substances remain uncharacterised (Bohacek et al., "The Art and Practice of Structure-Based Drug Design: A Molecular Modeling Perspective", 1996, Med. Res. Rev., 16 (1), p 3-50).

Therefore, all of the approaches described above are severely negatively affected when no or limited mass spectral data is available for a substance. Moreover, the large number of structures that are chemically feasible (even for small molecular formulae) means that computational complexity can become problematic in methods that attempt to build superstructures or predict fragmentation patterns of large molecules. It would be desirable if identifying substances quickly and accurately were possible using mass spectrometry alone, without requiring further specialist equipment and knowledge.

SUMMARY OF THE INVENTION

Against this background, the present disclosure provides a method for analysing mass spectral data of a substance.

The present disclosure further provides a computer program and a mass spectrometry system.

A method according to the present disclosure comprises: identifying a plurality of candidate chemical structure sets for a substance, each set being identified using one or more respective properties of mass spectral data; and determining a level of similarity between candidate chemical structures from different candidate chemical structure sets, so as to determine a likelihood that one of the candidate chemical structures represents the substance.

In other words, the present disclosure relates to a method of identifying potential chemical structures for an unknown substance by performing two (or more) independent searches based on different properties of mass spectral data obtained from the unknown substance. The mass spectral data is preferably a mass spectrum of the unknown substance. Once a number of potential chemical structures are identified, the potential chemical structures obtained from the different searching methods may then be compared so as to determine how similar they are. This comparison may be used to determine whether the identified chemical structures are likely to represent the unknown substance. For instance, if two independent searches provide similar results, then the methods of the present disclosure may determine that the similar results are likely to be similar to the actual chemical structure of the unknown substance, because of the fact that two (or more) independent searching methods returned consistent results.

Thus, the disclosure may provide an efficient, general and reliable method for identifying exact or approximate chemical structures of substances using mass spectral data alone. Identifying chemical structure sets using different properties of mass spectral data may ensure that sensible, consistent chemical structures are identified for substances. This may eliminate (or at least reduce) much of the complexity of existing methods that seek to identify structures for substances using mass spectral data. For instance, some existing methods attempt to reconstruct superstructures from fragments, which may be unreliable and computationally expensive. The disclosure recognises that even if a query compound is not present in a mass spectral library, as long as the spectral search yields at least some similar spectra, then advantages may be provided by searching in a structure library for compounds that are similar (and not necessarily identical to) the structures returned from the spectral search. The relations between chemical structure and other physical, chemical and biological properties are central to chemoinformatics and specific models for their quantitative prediction are common tools in drug design, structure-activity relationships and many other areas (A. M. Johnson and G. M. Maggiora, "Concepts and Applications of Molecular Similarity", 1990, John Willey & Sons). Thus, the present disclosure's benefits may be exploited in a variety of scientific disciplines.

When compared to existing spectral libraries, public structure libraries typically hold several orders of magnitude more structure records, so the probability of finding the structure of the substance is increased significantly. Moreover, this approach has the additional benefit that further data sources can be added as and when they become available. For instance, if further databases of chemical structures are developed based on further properties of mass spectral data, then it is straightforward using the methods of the present disclosure to determine a measure of similarity between candidate chemical structures and further candidates identified from such further databases. Thus, the present disclosure provides an adaptable and effective method for improving the accuracy of identification that may be generally applicable to all databases of chemical structures characterised by various properties.

Preferably, the method further comprises identifying a candidate chemical structure set of the plurality of candidate chemical structure sets by searching a chemical structure library. Searching the chemical structure library may comprise: identifying a peak in the mass spectral data and a respective mass-to-charge ratio; and identifying a chemical structure in the chemical structure library as a candidate chemical structure when a mass-to-charge ratio of the chemical structure in the chemical structure library corresponds with the mass-to-charge ratio of the identified peak. Chemical structure libraries may hold far greater numbers of chemical structures than mass spectral libraries, thereby increasing the number of possible chemical structures for the substance. Furthermore, chemical libraries can include structural representations of substances that are as yet unobserved but which are nevertheless chemically feasible. Hence, the present disclosure may enable previously uncharacterised substances to be structurally elucidated in an efficient and accurate manner. Moreover, expanding the space of candidate chemical structures in this way means that structurally characterised substances can be used to determine candidate chemical structures based on the mass-to-charge ratio of a precursor ion in an $MS^2$ spectrum, even if no $MS^2$ mass spectral data for the precursor ion is available.

Advantageously, the disclosure may further comprise identifying a chemical structure in the chemical structure library as a candidate chemical structure when the mass-to-charge ratio of the chemical structure in the chemical structure library and the mass-to-charge ratio of the identified peak differ by no more than a tolerance value. Preferably, the chemical structure library comprises: at least one chemical structure representation of: a molecular ion; a fragment ion; a precursor ion comprising at least one molecular structure and at least one adduct; and a mass-to-charge ratio for each chemical structure representation. In other words, the chemical structure library may comprise representations of various uncharged molecules, and molecular ions, and fragments commonly encountered in mass spectrometry. Thus, the disclosure recognises that various chemical structures may, when combined with typical adducts, represent precursor ions in tandem mass spectral data. Hence, the disclosure may continue to operate effectively by accounting for possible adductions, which tend to make mass spectral data more difficult to interpret.

Preferably, the method additionally or alternatively comprises identifying a candidate chemical structure set of the plurality of candidate chemical structure sets by searching a mass spectral library. In this way, candidate chemical structures identified from a chemical structure library may be compared with candidate chemical structures identified from a mass spectral library. This cross-check may mean that even if the mass spectral data does not provide an exact match, an approximate structure for the substance may still be identified quickly and efficiently. Furthermore, if a candidate chemical structure is present in candidate chemical structure sets identified by independent database searches, then it may be inferred that the candidate chemical structure represents the substance.

The mass spectral data subjected to the library and structure searches are preferably representations of spectra acquired for the same polarity ions. For instance, the present disclosure may utilise data generated from mass spectrometry analysis such as conventional analysis data (i.e. data acquired for one ion polarity or the other), and subject the experimental mass spectra to library and structure searches to identify a molecular structure having the highest probability of matching the analyte. Using mass spectra for ions of the same polarity contrasts with methods that simultaneously generate positive and negative ions from a (single particle) sample, such that mass spectra of ions of opposite polarities can be concurrently acquired. Advantageously, using the methods of the present disclosure, there is no requirement for simultaneous generation of positive and negative ion spectra that are separately searched with subsequent combination of results. The methods of the disclosure can provide efficient searching methods that are generally applicable in a range of mass spectrometry methods.

Optionally, the mass spectral library comprises chemical structure representations of characterised chemicals and respective mass spectral library data. In this case, searching the mass spectral library may comprise: identifying a peak group in the mass spectral data, the peak group comprising peak group data; and identifying a characterised chemical in the mass spectral library as a candidate chemical structure when the identified peak group data corresponds with mass spectral library data of the characterised chemical. Hence, specific groups of peaks in mass spectral data can be used or an entire spectrum can be searched. Groups of peaks may comprise entire tandem mass spectra or specific groups of peaks that are suspected to represent a particular fragment of a substance.

Preferably, the mass spectral data is tandem or multi-stage, $MS^n$, mass spectral data. In this case, the peak group may also comprise a tandem or multi-stage, $MS^n$, mass spectrum. The fragmentation in a higher-energy collisional dissociation (HCD) spectrum may be viewed as an aggregation of all hypothetical tandem $MS^2$ collision induced dissociations (CID) of the same precursor ion. Following similar principles as in precursor ion fingerprinting (PIF), a characteristic fragmentation profile corresponding to a hypothetical precursor ion may be observed in structurally related compounds. The disclosure recognises that in contrast to tandem CID spectra, common fragmentation patterns are not isolated to individual spectra, but form a subset of all other fragmentations for that particular compound. This common subset of product ions then indicates the extent of the structural analogy between the parent compounds. Thus, in the context of spectral library searching, the disclosure expands searches to reference spectra that share the largest portion of the product ions with the query. A highly advantageous aspect of the disclosure is the concept of targeting similar, but not identical spectra, such as spectra of different compounds that may originate from diverse precursor ions, and which may have distinct overall dissociation profile with many non-overlapping m/z ranges.

The advantages of the disclosure may be particularly apparent when higher-energy collisional dissociation (HCD) mass spectrometry (i.e., beam-type collisional dissociation effected by acceleration of ions into a collision cell) is employed. This allows for multiple reactivation of intermediate fragments in the collision cell, thereby encouraging continuous dissociation and providing ample spectral data. Interpretation of such data has to date been extremely challenging due to the extremely large number of ions and potential fragmentation pathways. Nevertheless, in the context of the present disclosure, the use of HCD spectra comprising large numbers of distinct peaks may allow for higher specificity and reduce the ratio of false positives.

Preferably, identifying the characterised chemical in the mass spectral library as a candidate chemical structure comprises: determining a spectral similarity score indicating the extent to which the identified peak group data correspond with the mass spectral library data of the characterised chemical; and identifying the characterised chemical as a candidate chemical structure when the spectral similarity score satisfies a threshold condition. Thus, chemical structures are only identified as candidate chemical structures when an appropriate degree of spectral similarity is identified.

Advantageously, the spectral similarity score may be an asymmetric spectral similarity score indicating the proportion of the peak group data present in the mass spectral library data. Hence, it is possible to expand the searches to those reference spectra that share the largest portion of the product ions with the query. While conceptually similar to classic library searching, a key difference is targeting similar but not identical spectra. Comparing spectra for identity may penalise differences in peaks, so comparing for similarity in an asymmetric manner ensures that common peaks are rewarded in the overall ranking of candidate chemical structures. Moreover, fragmentation fingerprints of particular precursor ions are conserved between structurally related compounds. Thus, the isolation of activated ion breakdown steps into separate product spectra may yield a fragmentation fingerprint of the particular precursor ion. This may be particularly advantageous in embodiments of the disclosure in which similar, rather than exact, matches in the spectral library are identified.

Preferably, the present disclosure further comprises: identifying a plurality of groups of candidate chemical structures, each group of candidate chemical structures comprising one candidate chemical structure from each candidate chemical structure set and determining the level of similarity for each of the plurality of groups of candidate chemical structures. Combining a modified mass spectral library search with a structure search to identify groups of candidate chemical structures increases the likelihood of identifying the correct structure for the substance by ensuring that structures within each group are consistent, and penalising those groups that do not exhibit sufficient consistency. This may advantageously include generating ranked groups of chemical structures, further exploiting the similarities between spectra of structurally related fragments.

Preferably, the present disclosure further comprises determining the level of similarity for all groups of candidate chemical structures consisting of one candidate chemical structure from each candidate chemical structure set. Thus, the number of candidate chemical structures assessed is maximised, thereby reducing the risk of not identifying a correct chemical structure for the substance. In particular, the present disclosure preferably further comprises calculating, for each group of candidate chemical structures, a weighted product of: the spectral similarity score of the candidate chemical structure in the group of candidate chemical structures obtained by searching the mass spectral library; and the level of similarity of the group of candidate chemical structures. Weighting the product of spectral similarity score and the level of similarity identified between candidate chemical structures from different candidate structure sets ensure that appropriate candidate chemical structures are identified as likely structures for the substance.

The disclosure may further comprise: identifying the group of candidate chemical structures having the highest weighted product; and identifying a candidate chemical structure in the group of candidate chemical structures having the highest weighted product as a most likely chemical structure of the substance. Thus, groups comprising candidate chemical structures that have a mass spectral similarity score whilst exhibiting consistency within the group are most likely to be identified as the likely chemical structure for the substance.

Additionally, the present disclosure may further comprise combining the weighted products of groups of candidate chemical structures comprising a common candidate chemical structure, so as to determine a likelihood that the common candidate chemical structure represents the substance. In other words, the disclosure may identify two candidate chemical structure sets via independent methods (or properties of mass spectral data), identify a measure of likelihood for all combinations resulting from selecting one candidate chemical structure selected from each different sets, then combining (such as by summing over a particular candidate, for example) the determined measures of likelihood for all pairs comprising one particular candidate chemical structure identified from one of the independent methods. Thus, a sum of weighted products over a particular candidate chemical structure may be identified which may be particularly advantageous when tandem or multi-stage mass spectral data is used, since conserved symmetries between structural fragments may be exploited. For instance, if partial scores are summed over all spectral search results for a particular candidate structure identified from a structure search, then similarities between spectra of related fragments may be exploited.

Preferably, the present disclosure further comprises representing the candidate chemical structures graphically, wherein determining the level of similarity comprises determining a level of similarity between the graphical representations of the candidate chemical structures. Preferably, determining the level of structural similarity comprises identifying a maximal common substructure (MCS) between the candidate chemical structures. Thus, structurally sensible candidate chemical structures may be identified in a fast and reliable manner.

Additionally or alternatively, the present disclosure may further comprise representing the candidate chemical structures by descriptors, wherein determining the level of similarity between candidate chemical structures comprises determining a similarity measure between the descriptor representations of the candidate chemical structures. Descriptor-based methods may be more efficient than graphical methods, leading to reduced elucidation times.

Preferably, there is provided a computer program, configured when operated by a processor to carry out the described methods. Preferably, there is also provided a mass spectrometry system, comprising: a mass analyser, configured to provide mass spectral data for a substance; and a control/data system, configured to carry out the described methods using the mass spectral data provided by the mass analyser. The mass spectrometer system may comprise a single stage, tandem or multi-stage $MS^n$ mass spectrometer configured to perform one or more of: ion formation; ion selection; ion isolation; ion activation; ion separation; and ion detection.

BRIEF DESCRIPTION OF THE DRAWINGS

The disclosure may be put into practice in various ways, which will now be described by way of example only and with reference to the accompanying drawings in which.

DETAILED DESCRIPTION OF PREFERRED EMBODIMENTS

Aspects of the present disclosure are now described by reference to the accompanying Figures. Firstly, there is provided a description of a suitable hardware arrangement for implementing the methods described herein. Then, analytical methods of the disclosure are illustrated generally with reference to FIGS. 2, 3 and 4. Finally, a worked example is described by reference to FIGS. 5 to 8, in which it is illustrated how embodiments of the present disclosure may elucidate the chemical structure of an unknown substance using mass spectral data.

Suitable Hardware

Figure 1:
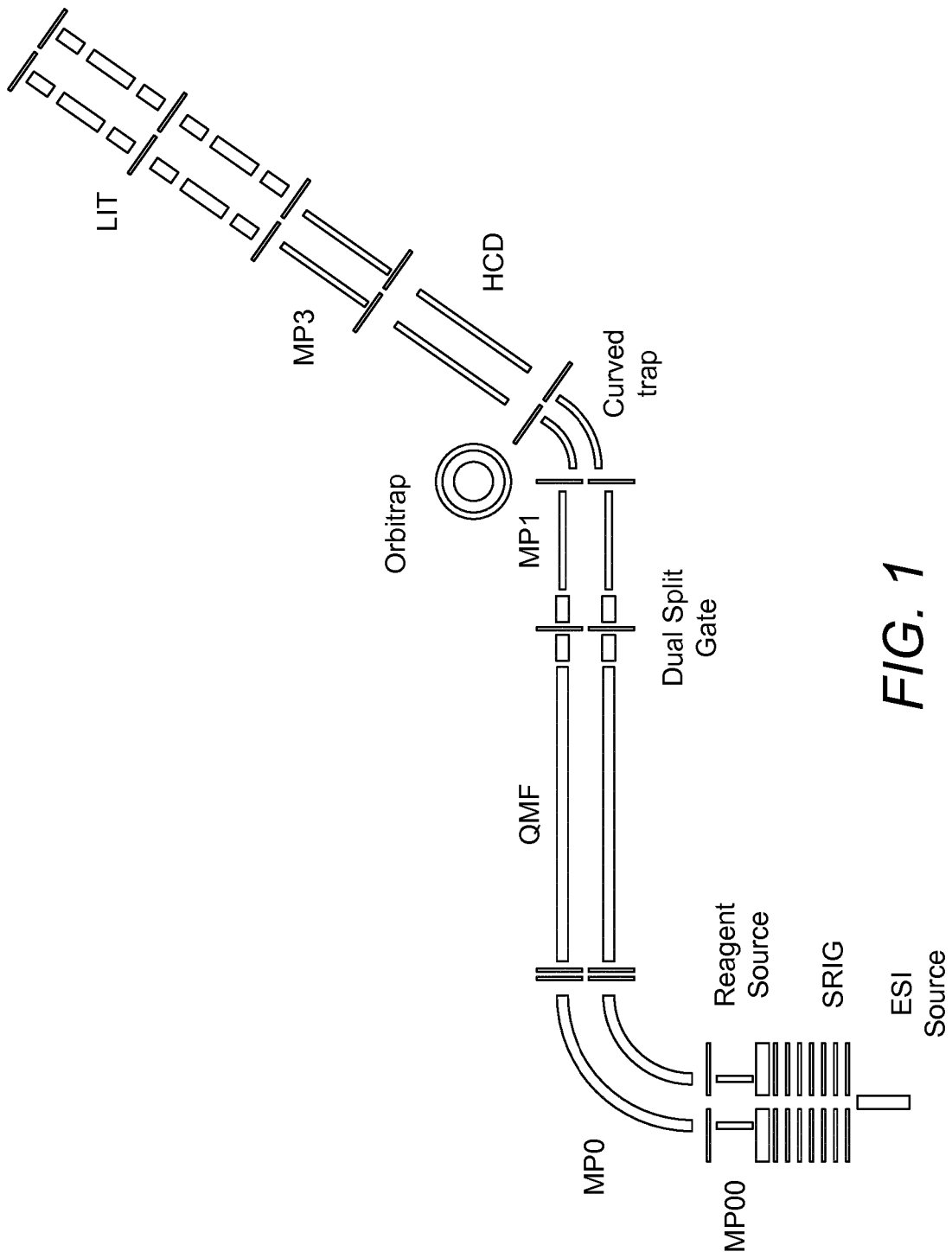
FIG. 1 is a schematic diagram of an exemplary known system, which may be configured to implement embodiments of the present disclosure.

Referring now to FIG. 1, there is shown a schematic diagram of an exemplary mass spectrometer, using which an embodiment of the present disclosure may be implemented. The hardware arrangement of FIG. 1 is suitable for producing $MS^n$ data and includes three different types of mass analysers, consisting of a quadrupole mass filter (QMF), an orbital trapping mass analyser (such as an Orbitrap, as provided by Thermo Fisher Scientific), and a linear (two-dimensional) quadrupole ion trap mass analyser (LIT). In operation, ions generated by an ion source (which may be an electrospray source, as depicted, but may alternately take the form of any other suitable structure for producing sample ions in a pulsed or continuous manner) are conveyed through a heated ion transfer tube, which assists in the evaporation of residual solvent, into a stacked ring ion guide (SRIG) of the type described in U.S. Pat. No. 7,514,673 B2. Application of RF voltages to the SRIG electrodes establishes an RF field that confines and focuses ions as they traverse the SRIG. The ions then pass through a short RF multipole ion guide MP00 and are conveyed through a curved multipole ion guide MP0 into the QMF. Curved multipole MP0 is preferably provided with structures for establishing a DC gradient along the central axis to assist in the transport of ions to the QMF. The QMF, which is conventionally constructed from four rod electrodes having hyperbolic surfaces, is operable to selectively transmit ions with a desired range of mass-to-charge (m/z) ratios. The transmitted m/z range is set by adjusting the amplitudes of the RF and resolving DC voltages applied to the rod electrodes, as is known in the art.

The ion stream emerging from the QMF is gated by a split gate lens into discrete packets for analysis by the orbital trapping or LIT analyser. The ion packets pass through another RF multipole ion guide MP1 and into a curved ion trap, which is constructed from rod electrodes curved concavely toward the entrance to the orbital trapping analyser.

This curved ion trap may be similar to the curved ion trap (referred to sometimes as a "C-trap") currently in use in commercially available orbital trapping instruments. Ion packets entering the curved ion trap are released through the opposite end to the higher-energy collisional dissociation (HCD) cell (also referred to as the "collision cell" or the "Ion routing multipole" or IRM), which operates to accumulate and optionally fragment the entering ions. The HCD cell takes the form of a multipole structure extending axially from a first to a second end, in which ions may be axially confined by adjusting voltages applied to the end lenses. The HCD cell may be, but is not necessarily, operated to produce fragmentation of ions delivered thereto. If fragmentation is desired, then the ions are accelerated into the HCD at the desired collision energy by adjusting the DC offset between the curved ion trap and/or other components upstream of the HCD cell; alternatively, if the ions are to remain intact, the DC offsets are adjusted to maintain the energies of the entering ions to a level at which no or minimal fragmentation occurs. The HCD cell may be filled with nitrogen, argon, or other suitable collision gas to cause fragmentation and/or assist in trapping.

Depending on the desired mode of analysis, ions accumulated (and optionally fragmented) within the HCD cell are passed either through its first end to the curved ion trap and thereafter to the orbital trapping analyser, or through its second, opposite end to multipole MP3 and thereafter to the LIT analyser. The direction in which ions are axially ejected from the HCD cell may be controlled by adjusting DC offsets applied to the end lenses and/or adjacent components, as well as by establishing an axial field (by means of auxiliary electrodes or other techniques or structures known in the art) that drives the ions toward the desired end. When analysis by the orbital trapping mass analyser is desired, the ion packet passes through the first end and is accumulated and confined within the curved ion trap. The ion packet is then orthogonally ejected from the curved ion trap and focused to the entrance of the orbital trapping mass analyser. The design and principle of operation of orbital trapping mass analysers such as the Orbitrap is well-known in the art and hence need not be described herein. Generally described, an orbital trapping mass analyser is an electrostatic trapping analyser constructed from inner and outer electrodes that establish a hyperlogarithmic field in which ions undergo harmonic motion along the longitudinal axis, the frequency of which is dependent on the square root of the m/z of the trapped ions. A mass spectrum of the trapped ions is acquired by detection of an image current on the split outer electrode, and the resultant signal (referred to as a transient) is converted to the frequency domain by a Fourier Transform and further processed to yield the mass spectrum.

Notably, the architecture of the mass spectrometer of FIG. 1, and in particular the placement of the HCD cell relative to the orbital trapping and LIT analysers, enables ions to be scanned (i.e., mass analysed) in either or both mass analysers while ions are accumulated in the HCD cell for the next series of scans. This parallelisation of ion accumulation and analysis enables efficient utilisation of the mass analysers and provides the ability to acquire more (or higher quality) data per unit time, relative to many commonly-used instruments.

The LIT analyser may take the form of the dual cell ion trap described in U.S. Pat. No. 7,692,142 B2, which is currently being sold by Thermo Fisher Scientific as the Velos linear ion trap. In this analyser, two linear trapping cells are placed adjacent one another and separated by an inter-cell ion optic or lens, which governs the flow of ions between the traps. The first ion cell (positioned proximate multipole MP3) is maintained at a pressure optimised for efficient trapping and fragmentation, while the second cell is maintained at a pressure optimised for mass analysis (which may be performed by mass sequentially ejecting ions to detectors located adjacent to ejection slots formed in the electrodes, in the manner known in the art). Each cell is constructed from four rod electrodes arranged in parallel around a central axis, with each rod electrode being segmented and having a hyperbolic-shaped surface facing the central axis. In a typical sequence, ions are initially trapped in the first cell, and the trapped ions are optionally subjected to one or more stages of isolation (in which all ions outside of a selected m/z range or ranges are ejected) and collisionally induced fragmentation (in which ions are energetically collided, via resonant excitation, with atoms or molecules of a collision gas added to the LIT interior). The resultant product ions (or precursor ions, if no fragmentation is performed) are then transferred to the second cell for acquisition of a mass spectrum. Inter-cell transfer of ions is effected by adjusting voltages applied to the inter-cell lens and the electrodes of the first and/or second cells, to thereby create a potential gradient that drives ions toward the second cell; alternatively, auxiliary electrodes may be employed to establish axial fields for this purpose.

For certain experiments, it may be beneficial to perform one or more stages of isolation and fragmentation in the LIT analyser (taking advantage of its $MS^n$ capabilities) followed by mass analysis of the resultant product ions in the orbital trapping analyser (taking advantage of its high resolution/accurate mass capabilities). In this case, the product ions are ejected from the LIT analyser through the entrance end of the first cell, and pass through the multipole ion guide MP3 and the HCD cell into the curved ion guide for accumulation thereby, with subsequent ejection to the orbital trapping analyser for mass analysis. If an additional stage of fragmentation is desired, then ions ejected from the LIT analyser are accelerated, by adjustment of DC offsets or by imposition of axial fields, to energies suitable to cause fragmentation within the HCD cell. Collisionally induced fragmentation within the HCD cell may offer certain advantages or opportunities relative to in-trap collisionally induced fragmentation, due to the wider range of collision energies available within the HCD cell and the lower low-mass cut-off associated with the HCD cell. In a variation of the foregoing experiment, ions may be ejected from the LIT analyser and accelerated into the HCD cell for fragmentation therein. The resultant product ions may then be returned (by adjustment of offsets or imposition of an axial field) to the LIT analyser for acquisition of a mass spectrum.

The LIT analyser may also be utilised to produce product ions via reactions with reagent ions, for example by electron transfer dissociation (ETD) or proton transfer reaction (PTR). For such experiments, reagent ions and sample (analyte) ions are sequentially injected into the LIT analyser. In the ETD example, ETD reagent ions, such as fluoranthene anions, are generated in a reagent ion source integrated into the exit lens of the SRIG. Such an ion source may utilise a Townsend discharge to ionise the fluoranthene molecules. The ETD reagent ions and sample ions are delivered, in turn, through the upstream components into the LIT analyser (since the polarities of the sample and reagent ions are opposite, the DC offsets applied to the components need to be adjusted to provide the appropriate gradients to drive ion flow). The sample and reagent ions are simultaneously trapped within the LIT analyser and allowed to mix, following an initial stage of separate confinement. The simultaneous confinement of oppositely charged ions within the LIT analyser may be achieved, for example, by application of oscillatory voltages to the end lenses or sections, as described in U.S. Pat. No. 7,026,613 B2. ETD product ions, resulting from the reaction of the reagent and sample ions, may then be mass analysed in either the LIT analyser or the orbital trapping mass analyser. Such mass analysis may be preceded by one or more additional stages of fragmentation or reaction, which may occur within the LIT analyser or the HCD cell. The reagent ion source may also be utilised to generate calibrant ions for use in calibrating the m/z measured by the mass analysers (i.e., as "lock mass" ions).

The mass spectrometer may be further capable of and/or configured to perform any one or more of ion formation, ion selection, ion isolation, ion activation, ion separation and ion detection techniques. The mass spectrometer will further include a control/data system (not depicted) for controlling the operation of the various components of the mass spectrometer and for processing and analysing data generated by the mass spectrometer, e.g., data representative of mass spectra acquired by one or more mass analysers. The functions of the control/data system may be distributed across multiple devices, which may include general-purpose and specialised processors, application-specific circuitry, programmable gate arrays, memory, non-volatile storage, input/output devices (e.g., displays, keyboards, positional input devices such as a mouse), and network interfaces for communicating with remote devices (e.g., to query libraries or databases stored on network computers or in a private or public computing cloud environment). Control/data system will preferably be provided with logic (for example, in the form of software instructions) for executing the steps of the methods described below. In any case, it will be appreciated that FIG. 1 is included for purposes of illustration only and that the methods of the present disclosure provide numerous advantages when employed in a variety of hardware arrangements.

Method of Analysis

Figure 2:
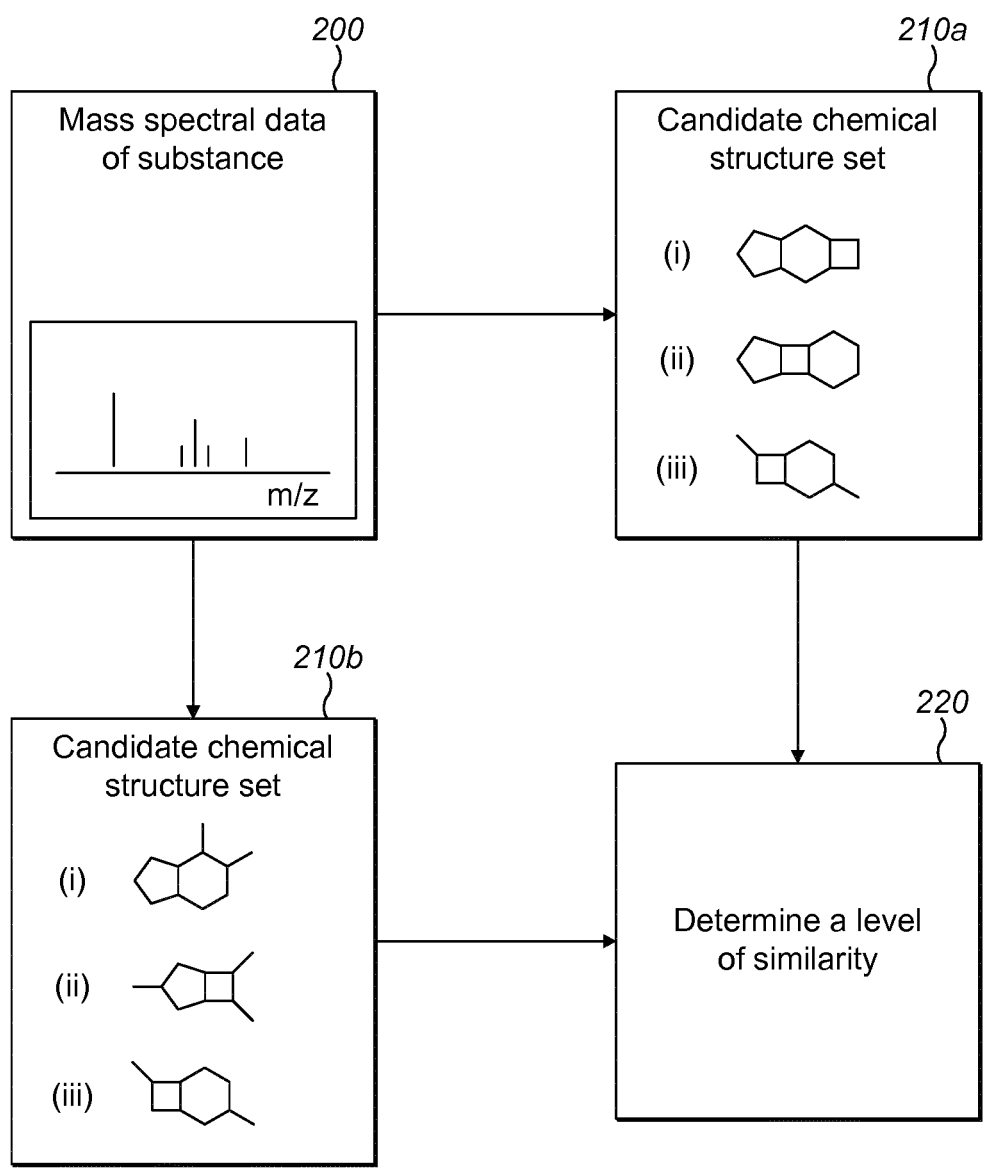
FIG. 2 is a schematic diagram of a method of analysing mass spectral data of a substance in an embodiment of the disclosure.

Referring now to FIG. 2, there is shown a schematic diagram illustrating a method of analysing mass spectral data 200 of a substance in accordance with an embodiment of the disclosure. The mass spectral data may be obtained from, for example, a mass spectrometer as illustrated in FIG. 1, although various other mass spectrometers may be utilised. The method of FIG. 2 comprises identifying a plurality of candidate chemical structure sets 210a and 210b using one or more respective properties of the mass spectral data. Then, the method of FIG. 2 comprises determining a level of similarity 220 between candidate chemical structures from different candidate chemical structure sets. The level of similarity may be indicative of, or may be used to infer, a likelihood that one of the candidate chemical structures represents the substance.

In the embodiment illustrated in FIG. 2, it can be seen that candidate chemical structure (iii) in candidate chemical structure set 210a appears to have the same structure as candidate chemical structure (iii) in candidate chemical structure set 210b. Therefore, the presence of this candidate chemical structure within candidate chemical structure sets that were obtained based on separate, independent properties of mass spectral data may be used to make an inference about the source of the mass spectral data 200. In particular, it may be inferred that the candidate chemical structure that is common to candidate chemical structure sets 210a and 210b is likely to represent, or at least be similar to, the chemical structure of the substance from which mass spectral data 200 was derived. Therefore, one or both of structures 210b(iii) and 210a(iii) may be inferred to be a likely chemical structure of a substance.

Whilst in FIG. 2 there is a candidate chemical structure, 210b(iii) and 210a(iii), that is common to each candidate chemical structure set, 210a and 210b, the present disclosure provides advantages even when no exact match is present. For instance, the determined measure of similarity may indicate a high likelihood of one of the candidate chemical structures representing (or at least approximately representing) the substance if the measure of similarity indicates that the candidate chemical structures are above a threshold similarity. This may be especially advantageous when attempting to identify, for example, a substances having a functional group with a distinctive mass spectral signature (such as, for example, a functional group having a particular isotopic fingerprint). In such cases, the presence in both candidate chemical structures of a functional group giving rise to the specific signature may be sufficient to confirm the identity and chemical structure of the substance. Thus, the embodiments of the disclosure are advantageous even when no exact matches are found from separate library searching methods.

For simplicity, two sets of candidate chemical structure sets are illustrated in FIG. 2, but it will be appreciated that further candidate chemical structure sets may be derived using further properties of the mass spectral data (or indeed from other data sources). Moreover, whilst in FIG. 2 there are two candidate chemical structure sets each comprising only three candidate chemical structures, each candidate chemical structure set may in fact comprise fewer or more than these numbers of candidate chemical structures. The number of candidate chemical structures within each set is not necessarily fixed and may be selected dynamically depending on the quality and number of potential candidate chemical structures that may be inferred from a particular property of the mass spectral data.

The embodiment of FIG. 2 may comprise combining a mass spectral library search with a structure search in a library of chemical structures. This may assist with elucidation of substances and may aid interpretation of mass spectral data even when known library searching methods are not suitable or are likely to yield poor results. Libraries of known (or feasible but not actually observed) chemical structures may hold far greater numbers of candidate chemical structures than mass spectral libraries. Thus, the use of such libraries may increase the chance of finding the correct (or at least approximate) structure of a substance. This may be achieved by associating the mass spectrum of the substance with a ranked set of chemical structures produced by a search of one or more libraries of chemical structures (described herein as a structure search) combined with a search of one or more mass spectral libraries (described herein as a spectral search).

The structure search may comprise searching for ions in a pre-constructed set or database of reference chemical structures, whose theoretical m/z values correspond to the m/z value of a precursor ion of the substance within its defined tolerance interval (i.e. the accuracy of the acquisition of the mass spectral data). The theoretical m/z may be calculated based on the monoisotopic molecular mass and a formal charge for the reference substance in the library, combined with one or more m/z values for adducts commonly observed in mass spectrometry. Adduct ions may also be negative, such as when an analyte adducts with a negatively charged ion (such as Chlorine), leading to species such as [M+Cl]−. In this case, the chemical structure search may comprise summing the monoisotopic molecular mass with the masses of various known negatively charged groups. Negatively charged precursor ions may also be generated by loss of a positive ion (such as deprotonation), leading to negatively charged species such as [M–H]–. In order to identify correctly ions generated by loss of positive ions, molecular masses of positive ions that may be lost during fragmentation may also be subtracted from the reference for the calculation of m/z. Thus, the structure search step of the present disclosure may comprise adding the masses of common adducts to molecular masses of known chemical structures in the chemical structure library, in addition to or instead of subtracting the masses of common fragmentation losses from the molecular masses of known chemical structures in the chemical structure library.

The outcome of such a structure search would then be a set of molecular representations of candidate chemical structures whose m/z match, at least to within a tolerance value, the m/z of the precursor ion of the substance or the m/z of the molecular ion peak of a molecule. In other words, the structure search generates a first set of candidate chemical structures based on a first property of mass spectral data, where the first property of the mass spectral data used to generate the first candidate chemical structure set is the mass-to-charge ratio of the precursor ion (or the molecular ion). As a chemical structure library may comprise a large number of chemical structures having a particular m/z value, the structure search may provide a relatively large number of candidate chemical structures for the substance.

The spectral search may then yield a further set of candidate chemical structures comprising structurally characterised fragmentation spectra from searching a pre-built library of mass spectral data. In other words, the structure search generates a second set of candidate chemical structures based on a second property of mass spectral data, where the second property of the mass spectral data used to generate the second candidate chemical structure set is a mass spectral pattern or fingerprint (i.e. a set or group of peaks and their associated m/z values). Entries in a mass spectral library may be identified as candidate chemical structures only when a measure of spectral similarity (i.e. a spectral similarity score), indicating the extent of the analogy between the mass spectrum of the substance and the mass spectrum in the library record, satisfies a threshold (i.e. indicates a sufficient degree of spectral similarity). Therefore, the number of candidate chemical structures for the substance may vary depending on the number of available spectra that sufficiently correspond with the mass spectral data. Whether two (or more) spectra correspond may be determined in the basis of the calculation of a spectral similarity score, which may be symmetric, encompassing common elements of the features present in both spectra, or asymmetric, indicating the extent to which one spectrum resembles the other.

Figure 3:
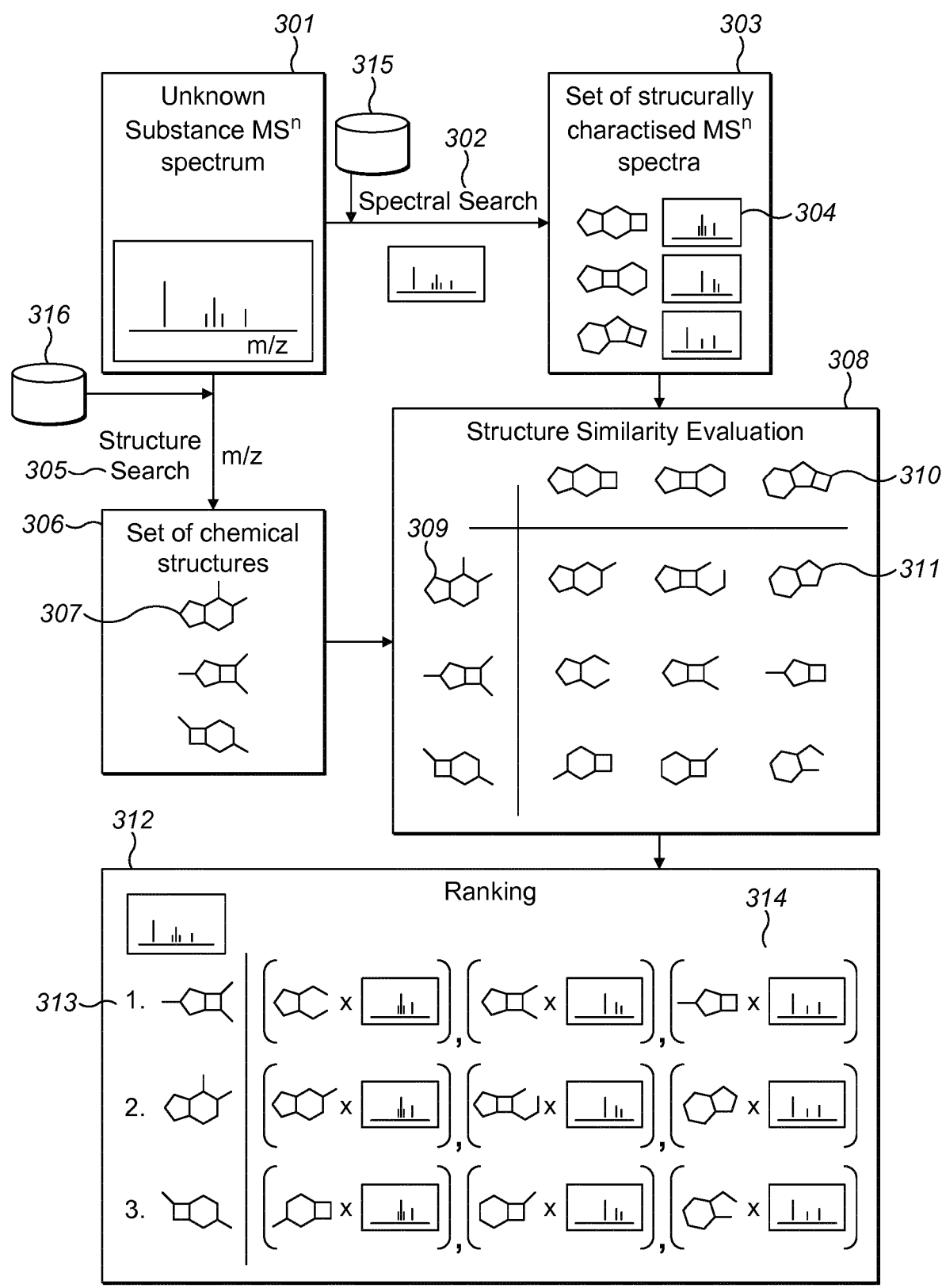
FIG. 3 is a schematic view of a method of identifying a substance in a preferred embodiment.

In FIG. 3 there is an illustration of one such embodiment of the disclosure. An $MS^n$ spectrum of a substance 301 is acquired by performing mass spectrometry with one or more stages of fragmentation, where at each stage of the fragmentation, a precursor ion of the substance is isolated and subsequently activated to produce fragmentation spectra. Any method of ion activation, such as collision induced dissociation (CID) or HCD, may be used. Whilst in FIG. 3 there is shown tandem or multi-stage $MS^n$ mass spectral data, this is simply for purposes of illustration. The method may also be employed advantageously by performing full MS with no additional fragmentation steps (i.e. using single stage MS) to obtain the mass spectral data.

In this embodiment, a spectral search 302 is performed, in which a set of structurally characterised $MS^n$ spectra 303 is identified, which form a first candidate chemical structure set 303 of structurally elucidated $MS^n$ spectra 304 assembled from a mass spectral library 315. The first candidate chemical structure set 303 comprises representations of substances whose mass spectra are sufficiently similar to the $MS^n$ spectrum of the substance 301 to warrant inclusion in the candidate chemical structure set.

The structurally defined $MS^n$ spectra 304 in the first candidate chemical structure set 303 may be ordered based on a quantitative measure of their spectral similarity with respect to $MS^n$ spectrum 301, such as a spectral similarity score, for instance. Whether the degree of similarity of a given pair of spectra is sufficient to warrant inclusion in the first candidate chemical structure set 303 may be assessed based on: user-specified spectral similarity thresholds; statistical analysis of likelihood of a match inferred using the spectral similarity; a predefined number of $MS^n$ spectra having the highest degree of similarity; or any other selection strategy. The spectral similarity score used may be a similarity index indicating the extent to which the $MS^n$ spectrum of the substance 301 resembles the library spectrum or vice versa.

The mass spectral library 315 used in the spectral search 302 may be any existing or tailor-made register of mass spectral data that comprises $MS^n$ spectra together with associated chemical structure representations. Existing public spectral libraries such as mzCloud or NIST may be used, and user-made spectral libraries may be used in addition to or instead of existing mass spectral libraries. The chemical structure representations in the mass spectral library may be graph-based and/or descriptor-based.

The embodiment of FIG. 3 further comprises a structure search step 305, in which the m/z value of a precursor ion of the $MS^n$ spectrum of the substance 301 is used to identify a set of chemical structures, which form a second candidate chemical structure set. The second candidate chemical structure set is identified from a database or library 316 of defined chemical substances that includes representations of various chemical structures and associated m/z values.

The database or library 316 may include further information about chemically feasible substances such as the number and type atoms and bonds present, theoretical monoisotopic mass, formal charge data, and any information pertaining to the substance (e.g. name, identifier, chemical class). The m/z of the substance may be calculated by combining the substance with a selected ion from a set of ionic adducts, comprising for example proton, single electron, ammonium, sodium cation, and any other adducts commonly encountered in mass spectrometry. The combination may result in subtracting species from the substance [M], for example [M–H]–, or any combination thereof. If the substance is itself an ion, additional adduct ion modification is optional. Any database of chemical substances may be used, such as PubChem, ChemSpider®, or a user-supplied set of substances, or any combination thereof. Methods such as those disclosed in, for example, U.S. Pat. No. 7,271,384 B2, may also be used.

It will be appreciated that the m/z value of the precursor ion (possibly including an adduct) of the $MS^n$ spectrum 301, together with the experimental tolerance of the instrumentation employed for the acquisition of the $MS^n$ spectrum 301, defines an interval of m/z values suitable for identifying candidate chemical structures. Chemical structures having m/z values that fall within this interval may represent the structure of a precursor ion or molecular ion. The instrument tolerance may be adjustable, specified by a user, detected by analysing the MS" spectrum 301, set to a predefined value, or set to an appropriate value in any other way. Furthermore, the tolerance may be adjusted so as to ensure that an acceptable number of candidate chemical structures are identified. Hence, selection of the second candidate structure set comprises identifying defined chemical substances as candidate chemical structures 307 when their m/z values, which may be calculated as the ratio of their theoretical monoisotopic masses to a molecular charge, fall within the m/z interval defined by the precursor ion of the MS" spectrum of the substance 301 and the instrument tolerance. Similar methods such as those disclosed in, for example, U.S. Pat. No. 7,349,809 B2 may be used.

When a plurality of candidate chemical structure sets have been identified, the embodiment of FIG. 3 proceeds to a candidate similarity evaluation step 308. In FIG. 3, the similarity evaluation comprises determining a level of structural similarity 311 between each element of the first candidate chemical structure set 303 and each element of the second candidate chemical structure set 306.

In all embodiments of the disclosure, representations of chemical structures may be graphical, descriptor-based, or a combination thereof. Graphical representations are graph theoretical mathematical structures describing pairwise relations or edges (representing bonds) between nodes or vertices (representing atoms). In other words, graphical representations are not typically pixel-based in the present disclosure. Possible categories of bonds comprise bond types such as single, double, triple, aromatic, whilst possible categories for atoms comprise atom properties such as elements, isotopes, formal charge and so on. In contrast, descriptor-based representations of a substance transform the chemical structures into objects whose similarity can be easily quantified, such as n-dimensional vectors, where each component of the vector encodes specific structural feature. For instance, they may define structures in terms of information such as substance identifiers, physical and/or chemical properties, compound class, and other properties. Other properties may include, for example, the number of aromatic atoms present, the total charge of the substance, and/or the number of atoms capable of forming hydrogen bonds. The degree of similarity 311 between representations of candidate chemical structures can be expressed in various ways. For instance, the identity and substructure relationships are relatively straightforward and fast methods for quantifying similarity, but suffer from a number of drawbacks. For instance, such binary classifications are rigid and produce high numbers of false negatives, particularly in cases when the structures of interest are very similar, but neither is a full substructure of the other.

A particularly advantageous embodiment of the disclosure comprises identifying the maximal common substructure (MCS) in similarity evaluation step 308, in the case that a graphical representation of the candidate chemical structures is adopted. The MCS is defined as the largest substructure contained within all of the compared structures and MCS produces a structural fragment that may be quantified by expressing the relative size of MCS to the reference structure. Identifying the MCS for arbitrary structures has been shown to be NP-complete, which has prevented its widespread use in cheminformatics and related applications in favour of less computationally intense methods. Moreover, whilst algorithms attempting to solve the MCS problem have been proposed (Conte et al., "Thirty years of graph matching in pattern recognition", 2004, Int. J. Patt. Recog. and Art. Int., 18 (03), p 265-298), these generally perform poorly for the types of graphs that are commonly encountered in chemical representations. Hence, to date, the power of the MCS has not been fully harnessed in the task of chemical identification or in analysis of mass spectral data.

A particularly powerful embodiment of the present disclosure is shown in FIG. 3, where respective candidate chemical structures are represented as graphs, and so the level of structural similarity between two candidate chemical structures may be expressed in terms of the relative size of the maximal common substructure (MCS) 311 of the pair of candidate chemical structures. Mathematically, the MCS may be quantified with respect to one of the respective candidate chemical structures 309 or 310, as a ratio of common bonds, atoms, or a combination thereof.

In embodiments in which candidate chemical structures are represented by descriptors, the similarity evaluation step 308 may instead comprise determining a distance or similarity measure 311 defined over a set of common features of the candidate chemical structures. Appropriate quantitative similarity measures include Tanimoto and Jaccard distances, for instance. Whilst these measures of similarity are more computationally effective than MCS, they may fail to account for well conserved local similarities in structures of different sizes, which may lead to an increased number of false negatives. In the context of mass spectrometry, such local similarities are likely to produce analogous fragmentation and descriptor-based methods may penalise such pairs of structures despite producing similar characteristic spectral fingerprints. Nevertheless, the descriptor-based methods may be performed exceptionally quickly, which is means that such methods are highly advantageous.

In any case, once a determination has been made as to the level of similarity between all different pairs of candidate chemical structures selected from the first and second candidate chemical sets, the results may be further analysed in a ranking step 312. In some embodiments, the pair (or group, when more than two candidate chemical structure sets are identified) of candidate chemical structures exhibiting the highest degree of similarity are identified as likely structures for the substance from which mass spectral data 301 was derived. This embodiment of the disclosure recognises that pairs of chemical structures identified via two independent searches and which also exhibit a significant degree of similarity, are more likely to represent the substance than candidate chemical structures that each appear to be potential structures for the substance based on their respective library searches but which have relatively few structural features in common. This embodiment effectively cross-checks for consistency between candidate chemical structures identified from separate sources.

Alternatively, the ranking step 312 may comprise ranking the candidate chemical structures in the second set 306 by summing partial similarity scores 314 over each candidate chemical structure in the first candidate chemical structure set 303. In this case, each partial score 314 may be calculated based on the similarity measure 311 and the spectral similarities of the respective candidate chemical structures from the first candidate chemical structure set 303. For instance, each partial score may be a weighted product of a spectral similarity score and the measure of similarity between the different candidate chemical structures from step 308. In other words, for each distinct pair of structure search 305 and spectral search 302 results, the structural similarity measure may be calculated as the manifestation of the structural features of the spectral search result 310 in the structure search results 307. The result is an ordered list of candidate chemical structures 313 that are ranked using partial scores 314 derived from pairs of candidate chemical structures. This approach may be particularly advantageous when tandem mass spectral data are used.

A particularly advantageous embodiment comprises determining a product of the squared spectral similarity score from step 302 and the similarity measure 311. This particular weighting (or indeed similar approaches) tends to penalise poor spectral similarity scores more heavily than a lack of similarity between candidate chemical structures, reflecting the importance of identifying a chemical structure as a likely structure for the substance only when a relatively high degree of spectral similarity is apparent.

Figure 4:
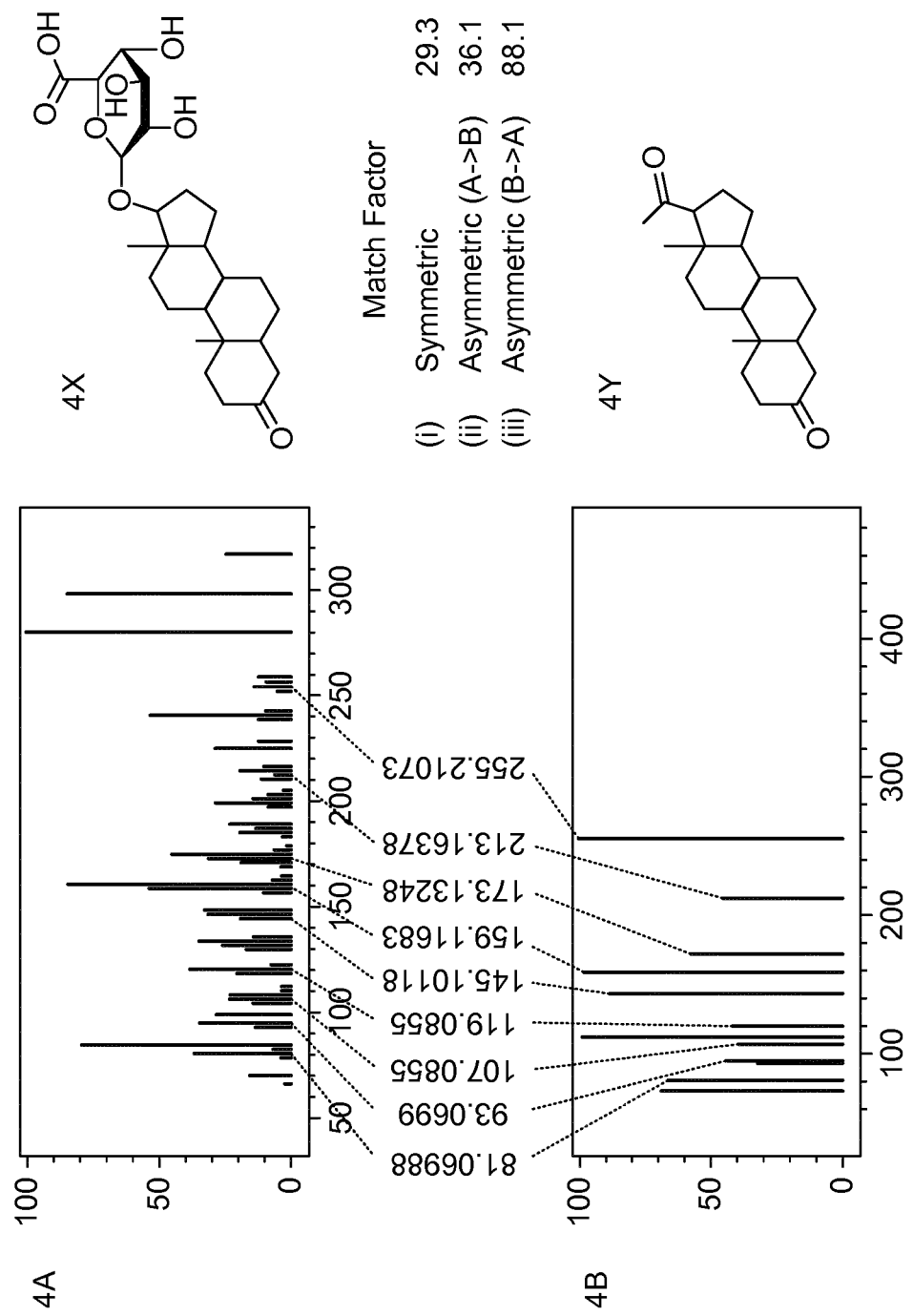
FIG. 4 is an illustration of methods of comparison of $MS^2$ ESI/HCD product ion spectra.

Embodiments of the disclosure compare sets of mass spectral data to determine a measure of similarity. Quantifying the degree of similarity between two sets of mass spectral data is not necessarily a trivial task, however. By way of example, there is shown in FIG. 4 an example of a spectral search that seeks to establish a measure of similarity between two spectra. The spectral comparison performed in FIG. 4 may be used to identify candidate chemical structures in step 302 of FIG. 3. In other words, the methods of FIG. 4 may be used to identify spectral similarity scores in any of the embodiments of the present disclosure.

There are in FIG. 4 shown two chemical structures of two structurally related compounds sharing a signature steroid substructure. In particular, 5a-Dihydrotestosterone glucuronide, 4X, is shown adjacent its corresponding mass spectrum 4A, and 5a-Pregnan-3,20-dione, 4Y, is shown adjacent its corresponding mass spectrum 4B. The mass spectral data in FIG. 4 may be ESI/HCD MS$^2$ fragmentation spectra.

Generally, the similarity between two mass spectra can be quantified by taking dot products between data structures that store quantised mass spectral data. However, there are several options for normalising and calculating such dot products. In each case, the final spectral similarity score may be expressed as a decimal number in the range [0,1], or as an equivalent percentage. Other normalisations may of course be used.

FIG. 4 is annotated to illustrate the peaks in spectrum 4B that have counterpart peaks in spectrum 4A. Despite the different overall distribution of the m/z values and abundances of the product ions, it is apparent that a distinct subset of peaks, denoted by their m/z, is common to both spectra and may be used to infer a partial overlap of the intermediate products in the respective dissociation pathways of 4X and 4Y. It may be particularly advantageous in certain embodiments of the disclosure to calculate spectral similarities in a directional fashion, whereby the peaks in one spectrum form the basis for the comparison with the other spectrum.

Symmetric match factor (i) is calculated as a dot product over the union of the peaks of both spectra and, as the majority of the peaks in 4A are not present in 4B, the overall match factor is low (29.3). The asymmetric (4A→4B) match factor (ii) is calculated over the entire 4A peak set and the corresponding 4B peak subset, essentially comparing all peaks present in 4A with complementary peaks in 4B. The slightly higher match factor (36.1) does not indicate a clear common fragmentation sub-pattern, as many peaks in 4A do not have counterpart peaks in 4B.

On the other hand, the asymmetric (4B→4A) match factor (iii) is much higher (88.1) because the majority of the peaks in 4B are contained also in 4A, indicating an overlap between a relatively large portion of the dissociation pathways of 4B and a smaller part of the dissociation pathway of 4A. This relationship between the fragmentation profiles correlates with the structural similarity of substances 4X and 4Y; a comparatively large portion of 4Y is a direct substructure of 4X. This asymmetric calculation may be particularly advantageous in embodiments of the disclosure.

Specific Example Overview

In FIGS. 5 to 8, there is shown a specific example of how the methods of the present disclosure may be used to assist in elucidating the MS$^2$ ESI/HCD high-resolution spectrum of penicillin-G. This example is not intended to limit the scope of the disclosure in any way.

As a first step in this example, a product-ion MS$^2$ ESI/HCD spectrum (shown in FIG. 5) is acquired for a precursor ion at m/z 335.1055 in a positive ion fragmentation mode.

Figure 5:
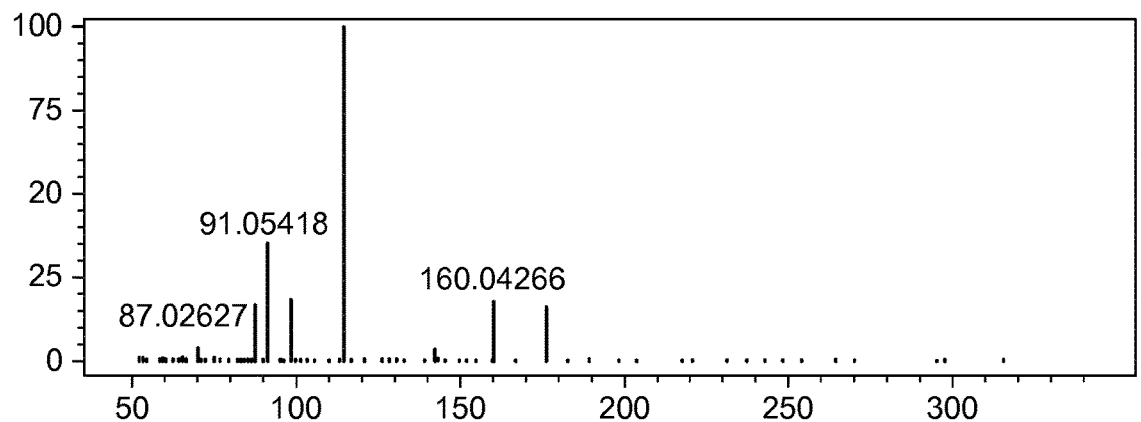
FIG. 5 is an example of a spectral search in a worked example.

As shown in FIG. 5, the m/z value of 335.1055 is accurate to +/−0.003Th. Thus, the second step of this example is a structure search for candidate chemical structures (and possible adducts) that correspond with this precursor ion m/z value to within instrument tolerance. In this particular example, a chemical structure library is searched for all chemical structures having m/z values in the range [335.1025, 335.1085]. In FIG. 5 there is also shown the structure search results (i), (ii) and (iii), together with exact theoretical m/z values and adducts that, when combined with chemical structures in a library, have theoretical m/z values that fall within the interval defined by the precursor ion m/z value and the instrument tolerance.

The input data required for the structure search in the worked example are the m/z of the precursor ion, its experimental accuracy and the polarity of the ion. These may be specified by a user, or automatically derived from mass spectral data files. Furthermore, the search may be restricted to specific subset of ion adduct types, such as adducts [M+H+] or [M+Na+], formed predominantly in positive ESI ionisations. For the sake of simplicity, in FIG. 5 only three structure search results are shown, corresponding to three different compounds whose [M+H+] or [M+Na+] adducts m/z fall into the interval defined by the precursor ion m/z and the instrument accuracy. It is further assumed for simplicity that the elucidated compound is present in the database used for the structure search, and that its precursor ion is indeed one of the specified adducts.

Figure 6:
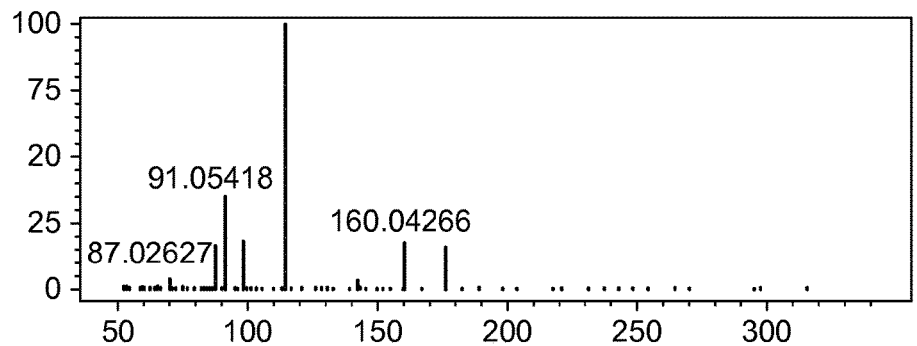
FIG. 6 is an example of a structure search in the worked example.
Figure 7:
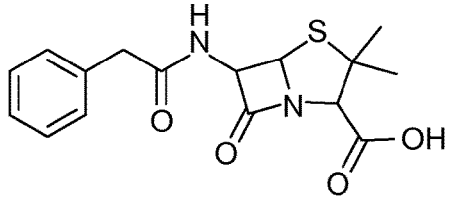
FIG. 7 is an example of partial score calculation in the worked example.
Figure 7:
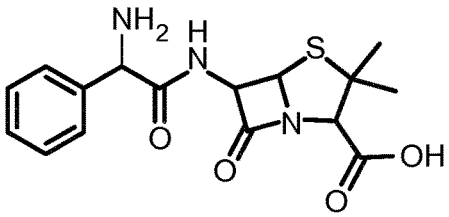
Figure 7:
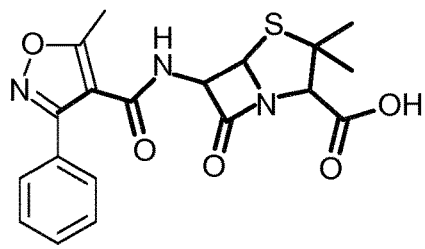
Figure 7:
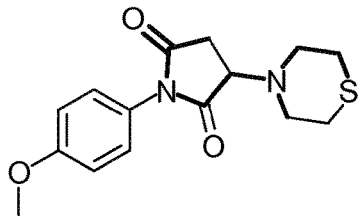

There are illustrated in FIG. 6 results of a spectral search in a pre-built mass spectral library on the basis of the MS$^2$ spectrum of the substance. Three distinct compounds (a), (b), and (c) with different masses are identified as producing analogous product-ion fragmentation spectra at the MS$^2$ stage. The "similarity" in FIG. 7 is a quantitative measure of the spectral similarity and is calculated based on the sum of dot products between all peaks from the elucidated spectrum, and corresponding peaks in the library spectrum. In other words, the similarity is calculated in an asymmetric manner by quantifying the extent to which the fragmentation profile of the substance is reflected in the library spectrum, disregarding any additional peaks observed in the library spectrum. However, any spectral similarity score described with reference to FIG. 4 may be used as the "similarity" in this step. These similarity measures may be expressed as percentages. For instance, the percentages may represent the relative size of the dot product with respect to the dot product that would be obtained by taking the dot product of one of the spectra (or the dot product using only peaks common to both spectra) with itself. Nevertheless, it will be appreciated that this normalisation convention is for illustrative purposes and that other normalisation conventions may be adopted.

The next step in the elucidation procedure comprises constructing a matrix of results from the structure search and spectral search results, as shown in FIG. 7. A single row of such a matrix is shown for structure search result (i) together with spectral search results (a), (b) and (c). For each pair of (i) with (a), (b) and (c), a structure similarity score is calculated using the MCS algorithm as the percentage of identical chemical bonds of (i) contained in (a), (b) or (c). Identical bonds are shown in bold in FIG. 7, for illustration. The spectral similarity scores in FIG. 7 are the scores from the spectral search shown in FIG. 6.

For each pair, a partial score is calculated as the product of the structural similarity score and the square of the spectral similarity score. It can be seen that the structure of (i) is a full subgraph of structure (a), so the structure similarity for pair (i,a) is 100%. This similarity, in combination with high spectral similarity score of (a), accounts for the highest contribution to the partial score for the pair. The second and third rows show corresponding similarity and partial score calculations for the (i,b) and (i,c) pairs. The MCS of the pair contains the characteristically fused β-lactam and thialolidine rings accounting for 76% of (i). Nevertheless, despite the slightly lower structural similarity score, the high degree of spectral similarity for the pair (i,b) translates into the second highest contribution ($0.76 \times 0.715^2$) to the partial score sum. Structure (c) shows little structural similarity to (i) (40%), as well as relatively low spectral similarity score (47%), which accounts for its overall small contribution ($0.4 \times 0.47^2$) of the (i,c) pair to the partial score sum. The partial scores for all pairs comprising (i) may thus be combined to give a partial score sum of 0.679. Alternatively, the partial scores may also be combined to give a partial score sum of 1.0439 by computing $1 \times 0.753^2 + 0.76 \times 0.715^2 + 0.4 \times 0.47^2$.

Figure 8:
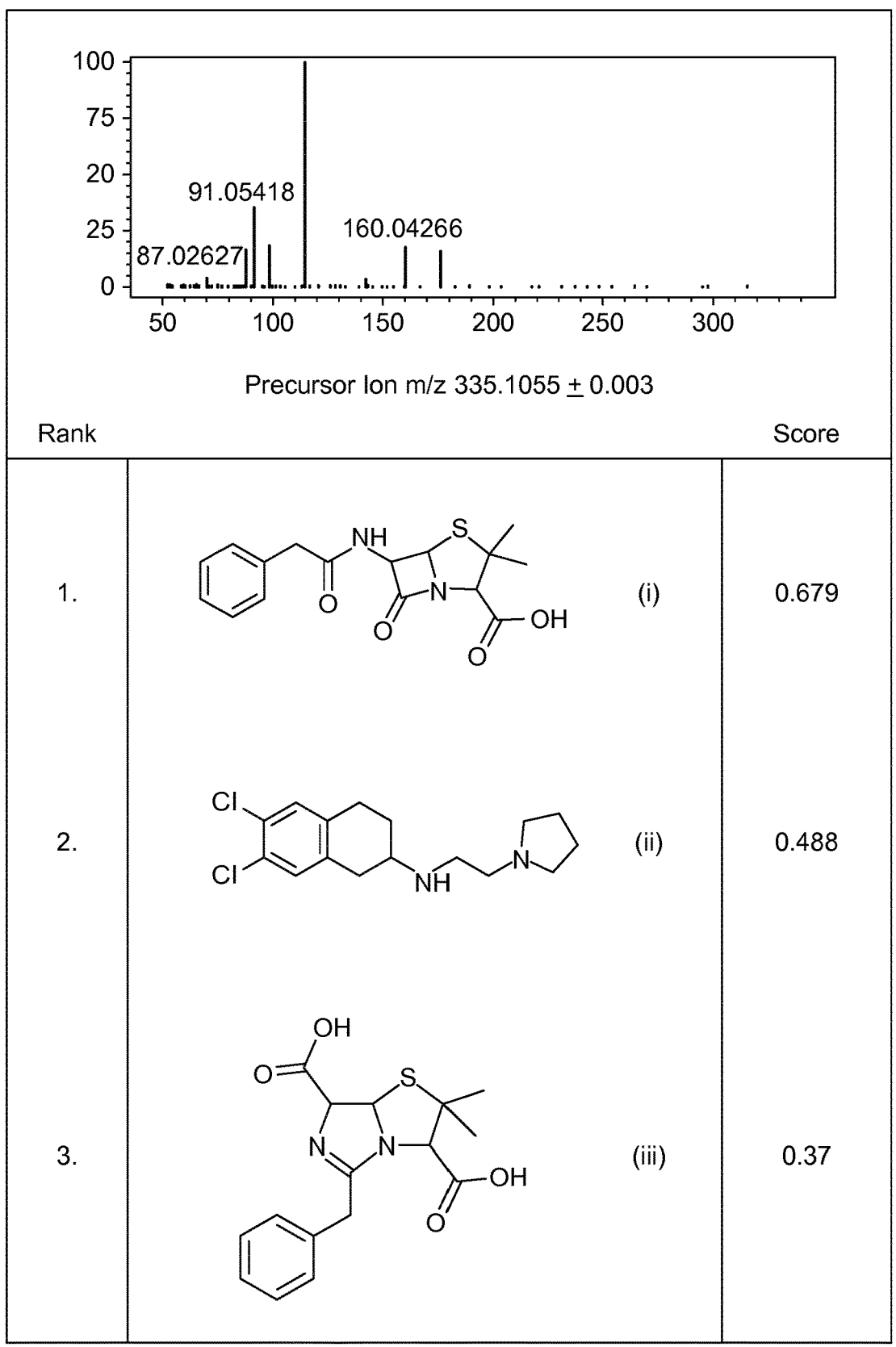
FIG. 8 is an example of the final ranking of results based on the sums of respective partial scores in the worked example.

Analogous procedures are carried out for structures (ii) and (iii) with respect to each of (a), (b) and (c), as shown in FIG. 8. Candidates (i), (ii) and (iii) for the elucidated precursor ion are ordered by their respective partial score sum. The correct structure (i) of penicillin-G is ranked first due to the prevalent contribution of the conserved spectral and structural patterns of penicillin derivatives identified by the mass spectral library search. In structures (ii) and (iii), the relatively poor MCS and product spectra penalised the individual products in the partial score sums and lowered their rank with respect to structure (i), leading to structures (ii) and (iii) scoring 0.488 and 0.37 respectively. Hence, structure (i) is correctly identified as the most likely chemical structure for the elucidated substance in this example.

Although the disclosure has been described with reference to particular types of data, devices and applications, and whilst the disclosure provides particular advantages in such cases, as discussed herein the disclosure may be applied to other types of data, devices and applications. Each feature disclosed in this specification, unless stated otherwise, may be replaced by alternative features serving the same, equivalent or similar purpose. Thus, unless stated otherwise, each feature disclosed is one example only of a generic series of equivalent or similar features.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" (such as a candidate chemical structure) means "one or more" (for instance, one or more candidate chemical structure). Throughout the description and claims of this disclosure, the words "comprise", "including", "having" and "contain" and variations of the words, for example "comprising" and "comprises" or similar, mean "including but not limited to", and are not intended to (and do not) exclude other components.

The use of any and all examples, or exemplary language ("for instance", "such as", "for example" and like language) provided herein, is intended merely to better illustrate the disclosure and does not indicate a limitation on the scope of the disclosure unless otherwise claimed. No language in the specification should be construed as indicating any non-claimed element as essential to the practice of the disclosure.

Any steps described in this specification may be performed in any order or simultaneously unless stated or the context requires otherwise.

All of the aspects and/or features disclosed in this specification may be combined in any combination, except combinations where at least some of such features and/or steps are mutually exclusive. In particular, the preferred features of the disclosure are applicable to all aspects of the disclosure and may be used in any combination. Likewise, features described in non-essential combinations may be used separately (not in combination).

The invention claimed is:

1. A mass spectrometry system, comprising:
a mass analyser, configured to provide mass spectral data for a substance; and
a control/data system, configured to perform the steps of:
identifying a plurality of candidate chemical structure sets for the substance, each set being identified using one or more respective properties of the mass spectral data, wherein identifying the plurality of candidate chemical structure sets for the substance comprises identifying a first candidate chemical structure set by searching a chemical structure library and identifying a second candidate chemical structure set by searching a mass spectral library comprising chemical structure representations of characterised chemicals and respective mass spectral library data;
identifying a plurality of groups of candidate chemical structures, each group of candidate chemical structures comprising one candidate chemical structure from each candidate chemical structure set; and
determining a level of similarity between candidate chemical structures from different candidate chemical structure sets for each group of candidate chemical structures, so as to determine a likelihood that one of the candidate chemical structures represents the substance.

2. A non-transitory computer readable medium comprising software instructions executable by a processor to carry out a method for analysing mass spectral data of a substance, the instructions comprising:
instructions to receive mass spectral data for a substance;
instructions to identify a plurality of candidate chemical structure sets for the substance, each set being identified using one or more respective properties of the mass spectral data, wherein the instructions to identify the plurality of candidate chemical structure sets for the substance comprise instructions to identify a first candidate chemical structure set by searching a chemical structure library and instructions to identify a second candidate chemical structure set by searching a mass spectral library comprising chemical structure representations of characterised chemicals and respective mass spectral library data;
instructions to identify a plurality of groups of candidate chemical structures, each group of candidate chemical structures comprising one candidate chemical structure from each candidate chemical structure set; and instructions to determine a level of similarity between candidate chemical structures from different candidate chemical structure sets for each group of candidate chemical structures, so as to determine a likelihood that one of the candidate chemical structures represents the substance.

3. The non-transitory computer readable medium of claim 2, wherein searching the chemical structure library comprises:

identifying a peak in the mass spectral data and a respective mass-to-charge ratio; and identifying a chemical structure in the chemical structure library as a candidate chemical structure when a mass-to-charge ratio of the chemical structure in the chemical structure library corresponds with the mass-to-charge ratio of the identified peak.

4. The non-transitory computer readable medium of claim 3, wherein the instructions further comprise instructions to identify the chemical structure in the chemical structure library as a candidate chemical structure when the mass-to-charge ratio of the chemical structure in the chemical structure library and the mass-to-charge ratio of the identified peak differ by no more than a tolerance value.

5. The non-transitory computer readable medium of claim 2, wherein the chemical structure library comprises:

at least one chemical structure representation of:
  a molecular ion;
  a fragment ion; and/or
  a precursor ion comprising at least one molecular structure and at least one adduct; and
a mass-to-charge ratio for each chemical structure representation.

6. The non-transitory computer readable medium of claim 2, wherein searching the mass spectral library comprises:

identifying a peak group in the mass spectral data, the peak group comprising peak group data; and identifying a characterised chemical in the mass spectral library as a candidate chemical structure when the identified peak group data corresponds with mass spectral library data of the characterised chemical.

7. The non-transitory computer readable medium of claim 6, wherein the mass spectral data is tandem or multi-stage, $MS^n$, mass spectral data, wherein the peak group comprises a tandem or multi-stage, $MS^n$, mass spectrum.

8. The non-transitory computer readable medium of claim 6, wherein identifying the characterised chemical in the mass spectral library as a candidate chemical structure comprises:

determining a spectral similarity score indicating the extent to which the identified peak group data correspond with the mass spectral library data of the characterised chemical; and identifying the characterised chemical as a candidate chemical structure when the spectral similarity score satisfies a threshold condition.

9. The non-transitory computer readable medium of claim 8, wherein the spectral similarity score is an asymmetric spectral similarity score indicating the proportion of the peak group data present in the mass spectral library data.

10. The non-transitory computer readable medium of claim 2, wherein the instructions further comprise instructions to determine the level of similarity for all groups of candidate chemical structures consisting of one candidate chemical structure from each candidate chemical structure set.

11. The non-transitory computer readable medium of claim 2, wherein the instructions to identify the second candidate chemical structure set of the plurality of candidate chemical structure sets by searching the mass spectral library comprise:

instructions to identify a peak group in the mass spectral data, the peak group comprising peak group data;

instructions to identify a characterised chemical in the mass spectral library as a candidate chemical structure by determining a spectral similarity score indicating the extent to which the identified peak group data correspond with the mass spectral library data of the characterised chemical and to identify the characterised chemical as a candidate chemical structure when the spectral similarity score satisfies a threshold condition; and instructions to calculate, for each group of candidate chemical structures, a weighted product of:

the spectral similarity score of the candidate chemical structure in the group of candidate chemical structures obtained by searching the mass spectral library; and the level of similarity of the group of candidate chemical structures.

12. The non-transitory computer readable medium of claim 11, wherein the instructions further comprise:

instructions to identify the group of candidate chemical structures having the highest weighted product; and instructions to identify a candidate chemical structure in the group of candidate chemical structures having the highest weighted product as a most likely chemical structure of the substance.

13. The non-transitory computer readable medium of claim 11, wherein the instructions further comprise instructions to combine the weighted products of groups of candidate chemical structures comprising a common candidate chemical structure, so as to determine a likelihood that the common candidate chemical structure represents the substance.

14. The non-transitory computer readable medium of claim 2, wherein the instructions further comprise instructions to represent the candidate chemical structures graphically, wherein determining the level of similarity comprises determining a level of similarity between the graphical representations of the candidate chemical structures.

15. The non-transitory computer readable medium of claim 14, wherein determining the level of structural similarity comprises identifying a maximal common between the candidate chemical structures.

16. The non-transitory computer readable medium of claim 2, wherein the candidate chemical structures are represented by descriptors, and wherein determining the level of similarity between candidate chemical structures comprises determining a similarity measure between the descriptor representations of the candidate chemical structures.

* * * * *